(12) United States Patent
Poinsard

(10) Patent No.: US 8,420,681 B2
(45) Date of Patent: Apr. 16, 2013

(54) DIOXO-IMIDAZOLIDINE DERIVATIVES, WHICH INHIBIT THE ENZYME SOAT-1, AND PHARMACEUTICAL AND COSMETIC COMPOSITIONS CONTAINING THEM

(75) Inventor: Cédric Poinsard, Le Plan de Grasse (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 13/202,663

(22) PCT Filed: Feb. 26, 2010

(86) PCT No.: PCT/EP2010/052495
§ 371 (c)(1),
(2), (4) Date: Oct. 6, 2011

(87) PCT Pub. No.: WO2010/097465
PCT Pub. Date: Sep. 2, 2010

(65) Prior Publication Data
US 2012/0021016 A1  Jan. 26, 2012

Related U.S. Application Data
(60) Provisional application No. 61/202,418, filed on Feb. 26, 2009.

(30) Foreign Application Priority Data
Jun. 5, 2009  (FR) .................................... 09 53753

(51) Int. Cl.
*A61K 31/4166* (2006.01)
*C07D 233/78* (2006.01)
(52) U.S. Cl.
USPC ....................................... 514/386; 548/311.1
(58) Field of Classification Search .................. 514/386; 548/311.1
See application file for complete search history.

(56) References Cited

U.S. PATENT DOCUMENTS

| | | | |
|---|---|---|---|
| 4,623,663 A | 11/1986 | Pittz et al. | |
| 5,003,106 A | 3/1991 | De Vries | |
| 5,106,873 A | 4/1992 | O'Brien et al. | |
| 5,159,114 A | 10/1992 | Bridge | |
| 5,338,849 A | 8/1994 | Festal et al. | |
| 6,133,326 A | 10/2000 | Mayne | |
| 6,271,268 B1 | 8/2001 | Mayne | |
| 2007/0197617 A1 | 8/2007 | Chen et al. | |
| 2010/0273813 A1 | 10/2010 | Portal | |
| 2010/0274583 A1 | 10/2010 | Beraja et al. | |

FOREIGN PATENT DOCUMENTS

| | | |
|---|---|---|
| DE | 1032258 | 6/1958 |
| EP | 0293880 A1 | 12/1988 |
| EP | 0370740 A1 | 5/1990 |
| EP | 0424194 A2 | 4/1991 |
| EP | 0433662 A2 | 6/1991 |
| EP | 0557171 A1 | 8/1993 |
| EP | 1 203 767 A1 | 5/2002 |
| WO | WO 96/10559 A1 | 4/1996 |
| WO | WO 2005/034931 A1 | 4/2005 |
| WO | WO 2009/030747 A1 | 3/2009 |
| WO | WO 2009/030750 A1 | 3/2009 |
| WO | WO-2009/030747 A1 * | 12/2009 |

OTHER PUBLICATIONS

International Search Report (PCT/ISA/210) issued on Sep. 19, 2011 by European Patent Office as the International Searching Authority for International Application No. PCT/EP2010/052495.
Kharbanda et al., "Systemic Acyl-CoA: Cholesterol Acyltransferase Inhibition Reduces Inflammation and Improves Vascular Function in Hypercholesterolemia," Circulation, Feb. 2005, pp. 804-807.
Puglielli et al., "Alzheimer's disease: the cholesterol connection," Nature Neuroscience, Apr. 2003, pp. 345-351, vol. 6, No. 4.
Nikkari, "Comparative Chemistry of Sebum," The Journal of Investigative Dermatology, 1974, pp. 257-267, vol. 62, No. 3.
Stahl et al., "Monographs on Acids and Bases," Handbook of Pharmaceutical Salts: Properties, Selection, and Use, 2002: pp. 265-267; Chapter 12, Wiley-VCH.
Dunbar et al., "Synthesis and antioxidative properties of novel thiazolidinedione/imidazolidinedione compounds as retinoids," Pharmazie, 2002, pp. 438-441, vol. 7
Pinza et al., "Synthesis and Pharmacological Activity of a Series of Dihydro-1 H-pyrrolo[1,2-a]imidazole-2,5(3H,6H)-diones, a Novel Class of Potent Cognition Enhancers," J. Med Chem., 1993, pp. 4214-4220, vol. 36.
Coudert et al., "Synthèse et évaluation de l'activité sur le système nerveux central de nouvelle triaza-spircodécanediones," Pharm. Acta Helv., 1991, pp. 155-159, vol. 66, No. 5-6. English language summary included.
Usifoh, "Anticonvulsant activity of reaction products of 5,5-diphenylhydantoin with substituted methylene bromides," Arch. Pharm. Pharm. Med. Chem., 2001, pp. 366-368, vol. 334.
Davion, "Synthesis of Substituted 1,4-Benzoxazepin-3-One Derivatives," Heterocycles, 2004, pp. 1093-1112, vol. 63, No. 5.

(Continued)

*Primary Examiner* — Kamal Saeed
*Assistant Examiner* — Janet L Coppins
(74) *Attorney, Agent, or Firm* — SNR Denton US LLP

(57) ABSTRACT

Compounds of general Formula (I),

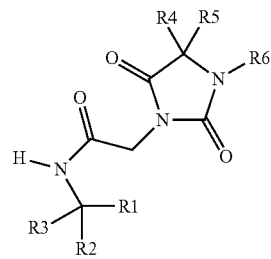

and cosmetic and pharmaceutical compositions containing such a compound are described.

31 Claims, No Drawings

OTHER PUBLICATIONS

Juaristi et al., "Enantioselective Synthesis of α-Amino Acids from Chiral 1,4-Benzodiazepine-2,5-diones Containing the α-Phenethyl Group," J. Org. Chem., 1999, pp. 2914-2919, vol. 64.

Matsumoto et al., "Multicomponent Strecker Reaction under High Pressure," Helvetica Chimica Acta, 2005, pp. 1734-1753, vol. 88.

Nieto et al., "Solution-Phase Parallel Synthesis of Spirohydantoins," J. Comb. Chem., 2005, pp. 258-263, vol. 7.

McOmie, "Protective Groups in Organic Synthesis," Protective Groups in Organic Chemistry, Plenum Press, 1973, pp. 10-15, 224-227, and 308-313, Edition 2.

White et al., "Heterocycle Amides: Inhibitors of Acyl-CoA: Cholesterol O-Acyl Transferase with Hypocholestrolemic Activity in Several Species and Antiatherosclerotic Activity in the Rabbit," J. Med. Chem., 1996, pp. 3908-3919, vol. 39.

O'Brien et al., "Inhibitors of Acyl-CoA: Cholesterol O-Acyltransferase. Synthesis and Pharmacological Activity of (±)-2-Dodecyl-α-phenyl-N-(2,4,6-trimethoxyphenyl)-2H-tetrazole-5-acetamide and Structurally Related Tetrazole Amide Derivatives," J. Med. Chem., 1996, pp. 2354-2366, vol. 39.

Goebel et al., "In search of Novel Agents for Therapy of Tropical Diseases and Human Immunodeficiency Virus," J. Med. Chem., 2008, pp. 238-250, vol. 51.

Feldman et al., "A Novel Route to the 4-Anilido-4-(Methoxycarbonyl)piperidine Class of Analgetics", J. Org. Chem., 1990, pp. 4207-4209, vol. 55.

Betts et al., "The Reactions of 1-Anilinocyclohexane-1-carboxylic Acid Synthesis of ψ-indoxylspiroxyclo-hexane," J. Chem. Soc., 1927, pp. 1310-1314.

Papadopoulos, "Reactions of Imidazoles with Isocyanates at Elevated Temperature," J. Org. Chem., 1977, pp. 3925-3929, vol. 42, No. 24.

Lada et al., "Identification of ACAT1- and ACAT2-specific inhibitors using a novel, cell-based fluorescence assay: individual ACAT uniqueness," Journal of Lipid Research, 2004. pp. 378-386, vol. 45.

Written Opinion of the International Searching Authority (Form PCT/ISA/237) issued on May 19, 2010, in International Patent Application No. PCT/EP2010/052495.

* cited by examiner

DIOXO-IMIDAZOLIDINE DERIVATIVES, WHICH INHIBIT THE ENZYME SOAT-1, AND PHARMACEUTICAL AND COSMETIC COMPOSITIONS CONTAINING THEM

This application is the United States national phase of PCT/EP2010/052495, filed Feb. 26, 2010, and designating the United States (published in the English language on Sep. 2, 2010, as WO 2010/097465 A1; the title and abstract were also published in English), which claims priority under 35 U.S.C. §119 of FR 0953753, filed Jun. 5, 2009, and U.S. Provisional Application 61/202,418 filed Feb. 26, 2009, each hereby expressly incorporated by reference in its entirety and each assigned to the assignee hereof.

The invention relates to novel dioxo-imidazolidine derivatives, which are inhibitors of the enzyme SOAT-1 (Sterol-O-Acyl Transferase-1, also known as ACAT-1: Acyl-coenzyme A Cholesterol Acyl Transferase). The invention also relates to the use of these derivatives in pharmaceutical compositions intended for use in human or veterinary medicine, or alternatively in cosmetic compositions, and also to their non-therapeutic use.

Compositions with activity of SOAT-1-inhibiting type are widely described in the literature as having activity in regulating biological processes involving cholesterol and derivatives thereof. These properties give this class of compounds strong potential in the treatment or prevention of many pathologies, and more particularly in dermatology and in cardiovascular diseases or central nervous system complaints. Most of the biological effects of SOAT-1 inhibitors are mediated by prevention of the synthesis of cholesterol esters by the enzyme SOAT-1. Among the prior art documents describing SOAT-1-inhibiting molecules, mention may be made, for example, of WO 96/10559, EP 0 370 740, EP 0 424 194, U.S. Pat. No. 4,623,663, EP 0 557 171, U.S. Pat. No. 5,003,106, EP 0 293 880, EP 0 433 662 and U.S. Pat. No. 5,106,873, which describe compounds for treating arteriosclerosis or hypercholesterolaemia. The therapeutic potential of SOAT-1 inhibitors in the treatment of cardiovascular diseases, and in particular of hypercholesterolaemia and arteriosclerosis, is also described by Kharbanda R. K. et al., in *Circulation*. 2005, 11, 804. The potential of SOAT-1 inhibitors for the treatment of Alzheimer's disease has also been reported in the literature, for example by Puglielli, L. et al., in *Nature Neurosciences* 2003, 6 (4), 345.

U.S. Pat. No. 6,133,326, U.S. Pat. No. 6,271,268 and WO 2005/034 931 describe SOAT-1-inhibiting compounds for inhibiting the production of sebum. In the field of dermatology, in particular, it is particularly advantageous to prevent excessive sebum production and all the associated conditions. Sebum is produced by the sebaceous glands. The largest concentration of sebaceous glands is found on the face, the shoulders, the back and the scalp. Sebum is secreted at the surface of the skin, where it plays a major physiological role, associated with maintaining the skin barrier and a microenvironment that permits regulation of the cutaneous bacterial and fungal flora.

Sebum hyperproduction is usually associated with a skin or scalp of greasy appearance, which is a cause of discomfort and of degraded appearance. Moreover, sebum hyperproduction may give rise to seborrhoeic dermatitis and is associated with an increased incidence or worsening of acne. The cholesterol esters produced in the sebaceous glands by SOAT-1 are one of the components of sebum, among several classes of lipids including triglycerides, wax esters and squalenes, as described by Nikkari, T., in *J. Invest. Derm.* 1974, 62, 257. Inhibition of this enzyme or of other acyl transferases may thus make it possible to inhibit sebum production. U.S. Pat. No. 6,133,326 especially describes the inhibition of sebum with ACAT-1 (also known as SOAT-1) inhibitors. However, at the present time, no treatment using such inhibitors is commercially available. The only treatments that can remedy or relieve hyperseborrhoea-related disorders are systemic hormonal treatments or systemic treatment with 13-cis-retinoic acid, the side effects of which treatments greatly limit their field of application. There is thus a clear medical and cosmetic need to treat complaints and pathologies related to sebum hyperproduction.

In this context, the present invention proposes to provide novel dioxo-imidazolidine derivatives that are powerful inhibitors of the enzyme SOAT-1.

One subject of the invention is novel dioxo-imidazolidine derivatives, which are inhibitors of the enzyme SOAT-1, and which correspond to the general formula (I) below:

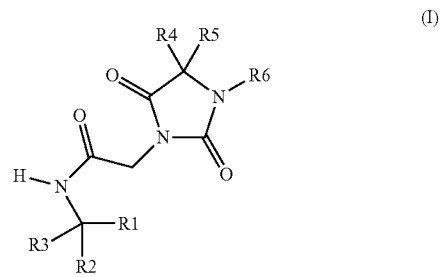

in which:
  $R_1$ and $R_6$ represent identical or different groups chosen from the following groups:
    aryl or naphthyl optionally substituted with one to three identical or different groups $R_a$,
    heteroaryl containing either a) from 1 to 4 nitrogen atoms or b) an oxygen or sulfur atom and 1 or 2 nitrogen atoms. These heteroaryls may be optionally substituted with one to three identical or different groups $R_a$,
  $R_2$, $R_3$, $R_4$ and $R_5$ are identical or different and represent:
    either a hydrogen atom,
    or a group $C_{1-6}$ alkyl optionally substituted with one to three groups $R_a$,
    or a group $C_{3-7}$ cycloalkyl, $C_{1-6}$ fluoroalkyl, $C_{1-6}$ fluoroalkyloxy or a group —$(CH_2)_n$—$C_{3-7}$ cycloalkyl,
  optionally, the groups $R_2$ and $R_3$ may form with the carbon atom that bears them a group $C_{3-7}$ cycloalkyl or a heterocycle such as tetrahydropyran-4-yl, tetrahydrothiopyran-4-yl, tetrahydro-1-oxythiopyran-4-yl or tetrahydro-1,1-dioxy-thiopyran-4-yl, piperidine optionally substituted on the nitrogen atom with a group $C_{1-6}$ alkyl, or azepan optionally substituted on the nitrogen atom with a group $C_{1-6}$ alkyl,
  optionally, the groups $R_4$ and $R_5$ may form with the carbon atom that bears them a group $C_{3-7}$ cycloalkyl or a heterocycle such as tetrahydropyran-4-yl, tetrahydrothiopyran-4-yl, tetrahydro-1-oxythiopyran-4-yl or tetrahydro-1,1-dioxythiopyran-4-yl, piperidine optionally substituted on the nitrogen atom with a group $C_{1-6}$ alkyl, or azepan optionally substituted on the nitrogen atom with a group $C_{1-6}$ alkyl,
  $R_a$ represents either a hydrogen, fluorine, chlorine or bromine atom or a group $C_{1-6}$ alkyl, $C_{3-7}$ cycloalkyl, $C_{1-6}$ alkyloxy, $C_{1-6}$ alkylthio, $C_{1-6}$ fluoroalkyl or $C_{1-6}$ fluoroalkyloxy, or a group —$(CH_2)_n$—$C_{3-7}$ cycloalkyl, OH, $CH_2OH$, $COOR_b$ or CN, $R_b$ represents a group $C_{1-6}$ alkyl, $C_{3-7}$ cycloalkyl or —$(CH_2)_n$—$C_{3-7}$ cycloalkyl, n is an integer equal to 1, 2 or 3, and also the pharmaceutically acceptable salts, solvates or hydrates thereof and the conformers or rotamers thereof.

The compounds of formula (I) may comprise one or more asymmetric carbon atoms. They may thus exist in the form of a mixture of enantiomers or of diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention. These salts are advantageously prepared with pharmaceutically acceptable acids, but the salts of other acids that are useful, for example for purifying or isolating the compounds of formula (I), also form part of the invention. These acids may be, for example, picric acid, oxalic acid or an optically active acid, for example a tartaric acid, a dibenzoyltartaric acid, a mandelic acid or a camphorsulfonic acid, and those that form physiologically acceptable salts, such as hydrochloride, hydrobromide, sulfate, hydrogen sulfate, dihydrogen phosphate, maleate, fumarate, 2-naphthalenesulfonate or para-toluenesulfonate. For a review of physiologically acceptable salts, see the *Handbook of Pharmaceutical Salts: Properties, Selection and Use* by Stahl and Wermuth (Wiley-VCH, 2002).

The solvates or hydrates may be obtained directly after the synthetic process, compound (I) being isolated in the form of a hydrate, for example a monohydrate or hemihydrate, or of a solvate of the reaction or purification solvent.

The present invention includes the isotopically labelled pharmaceutically acceptable compounds of formula (I) in which one or more atoms are replaced with atoms having the same atomic number but an atomic mass or a mass number different from the atomic mass or the mass number that naturally predominates. Examples of isotopes that may be included in the compounds of the invention include hydrogen isotopes such as $^2H$ and $^3H$, carbon isotopes such as $^{11}C$, $^{13}C$ and $^{14}C$, chlorine isotopes such as $^{36}Cl$, fluorine isotopes such as $^{18}F$, iodine isotopes such as $^{123}I$ and $^{125}I$, nitrogen isotopes such as $^{13}N$ and $^{15}N$, oxygen isotopes such as $^{15}O$, $^{17}O$ and $^{18}O$, phosphorus isotopes such as $^{32}P$ and sulfur isotopes such as $^{35}S$. Substitutions with isotopes that emit positrons, such as $^{11}C$, $^{18}F$, $^{15}O$ and $^{13}N$, may be useful in Positron Emission Tomography studies for studying the occupation of receptors.

In the context of the invention, the following definitions apply:

aryl: a monocyclic or bicyclic aromatic group containing 6 to 10 carbon atoms. Examples of aryl groups that may be mentioned include phenyl and naphthyl groups, $C_{b-c}$ in which b and c may take values from 1 to 6, a hydrocarbon-based chain of b to c carbon atoms, for example $C_{1-6}$ is a hydrocarbon-based chain that may contain from 1 to 6 carbon atoms, alkyl: a linear or branched saturated aliphatic group, for example a group $C_{1-6}$ alkyl represents a linear or branched hydrocarbon-based chain of 1 to 6 carbon atoms, for example a methyl, ethyl, n-propyl, isopropyl, n-butyl, isobutyl, tert-butyl, pentyl or hexyl, cycloalkyl: an optionally branched, cyclic saturated hydrocarbon-based chain containing from 3 to 7 carbon atoms, for example a cyclopropyl, cyclobutyl, cyclopentyl, cyclohexyl or cycloheptyl, heterocycle: a saturated or unsaturated cyclic or bicyclic hydrocarbon-based chain, comprising one or more heteroatoms chosen from O, S and N, heteroaryl: an aromatic heterocycle, for example these heteroaryl groups may be a pyridyl, pyrazinyl, pyrimidinyl, pyridazinyl, triazinyl, pyrazolyl, isoxazolyl, oxadiazolyl, thiazolyl, thiadiazolyl or triazolyl group, alkyloxy: a group —O-alkyl, alkylthio: a group —S-alkyl, fluoroalkyl: an alkyl group in which one or more hydrogen atoms have been replaced with a fluorine, fluoroalkyloxy: an alkyloxy group in which one or more hydrogen atoms have been replaced with a fluorine atom.

The preferred group of compounds of formula (I) defined above is the group (A), in which:

$R_2$ represents a hydrogen atom or a group $C_{1-6}$ alkyl, $C_{3-7}$ cycloalkyl, $C_{1-6}$ fluoroalkyl, $C_{1-6}$ fluoroalkyloxy or more favourably a hydrogen atom or a methyl, ethyl, isopropyl, propyl, cyclopropyl, $CH_2$-cyclopropyl or trifluoromethyl group and $R_3$ represents a methyl, ethyl, isopropyl, propyl, tert-butyl, cyclopropyl, $CH_2$-cyclopropyl or trifluoromethyl group, or more favourably $R_2$ is a hydrogen atom and $R_3$ represents a methyl, ethyl, isopropyl, propyl, tert-butyl, cyclopropyl, $CH_2$-cyclopropyl or trifluoromethyl group.

The group (B) of compounds of formula (I), the substituents $R_1$, $R_2$, $R_3$ and $R_6$ of which are defined above or in the preferred group (A) and such that the groups $R_4$ and $R_5$ independently represent an identical or different group $C_{1-6}$ or may form with the carbon atom that bears them a group $C_{3-7}$ cycloalkyl optionally substituted with either one or two fluorine atoms or an OH group or such that the groups $R_4$ and $R_5$ may form with the carbon atom that bears them a heterocycle such as tetrahydropyran-4-yl, tetrahydrothiopyran-4-yl or piperidin-4-yl optionally substituted with a group $C_{1-6}$ alkyl, $C_{3-7}$ cycloalkyl, is a group of preferred compounds, and more particularly preferred when $R_4$ and $R_5$ represent either a methyl, ethyl or propyl group or may form with the carbon atom that bears them a cyclopentyl, cyclohexyl or tetrahydropyran-4-yl group.

A particularly preferred group of compounds of formula (I) is group (C), the substituents $R_2$, $R_3$, $R_4$, $R_5$ and $R_6$ of which are defined above or in the preferred groups (A) or (B) and such that the group $R_1$ represents an aryl or naphthyl optionally substituted with one to three identical or different groups $R_a$ preferentially chosen from methyl, ethyl, propyl, isopropyl, cyclopropyl, $CH_2$-cyclopropyl, methoxy, ethoxy, propyloxy, isopropyloxy, fluoro, chloro, bromo, cyano, trifluoromethyl and trifluoromethyloxy groups and more particularly such that $R_1$ represents an aryl in which at least one of its substituents $R_a$ defined above is preferentially located in a meta position.

The group (D) of compounds of formula (I), the substituents $R_1$, $R_2$, $R_3$, $R_4$ and $R_5$ of which are defined above or in the preferred groups (A), (B) or (C) and such that $R_6$ represents an aryl, pyridyl, pyrazinyl, pyrimidinyl, pyridazinyl, triazinyl, pyrazolyl, isoxazolyl, oxadiazolyl, thiazolyl, thiadiazolyl or triazolyl group substituted with a group $R_a$ and most particularly such that $R_6$ represents an aryl group such as meta- or para-tolyl, meta- or para-methoxyphenyl, meta- or para-fluorophenyl, meta- or para-chlorophenyl or 3-pyridyl optionally substituted with one or more groups chosen from methyl, trifluoromethyl, fluoro, chloro, methoxy and $CH_2OH$, is a group of particularly preferred compounds.

The compounds below, and the pharmaceutically acceptable salts, solvates and hydrates thereof and the conformers or rotamers thereof, are particularly preferred:

N-benzyl-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-naphthalen-1-ylmethylacetamide;
2-(2,4-dioxo-1-p-tolyl-1,3-diazaspiro[4.5]dec-3-yl)-N-(3-trifluoromethyl-benzyl)acetamide;
2-(2,4-dioxo-1-p-tolyl-1,3-diazaspiro[4.5]dec-3-yl)-N-(1-phenylpropyl)acetamide;
2-(2,4-dioxo-1-p-tolyl-1,3-diazaspiro[4.5]dec-3-yl)-N—((R)-1-phenylpropyl)acetamide;
2-(2,4-dioxo-1-p-tolyl-1,3-diazaspiro[4.5]dec-3-yl)-N—((S)-1-phenylpropyl)acetamide;
2-(2,4-dioxo-1-p-tolyl-1,3-diazaspiro[4.5]dec-3-yl)-N-(1-o-tolylpropyl)acetamide;
2-(2,4-dioxo-1-p-tolyl-1,3-diazaspiro[4.5]dec-3-yl)-N-(1-o-tolylbutyl)acetamide;
2-(2,4-dioxo-1-p-tolyl-1,3-diazaspiro[4.5]dec-3-yl)-N-(2-methyl-1-o-tolylpropyl)acetamide;
2-(2,4-dioxo-1-p-tolyl-1,3-diazaspiro[4.5]dec-3-yl)-N-[1-(2-methoxyphenyl)butyl]acetamide;
2-(2,4-dioxo-1-p-tolyl-1,3-diazaspiro[4.5]dec-3-yl)-N-[1-(2-fluorophenyl)propyl]acetamide;
N-[1-(2,4-dimethylphenyl)propyl]-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-(1-p-tolylpropyl)acetamide;
N-[1-(4-chlorophenyl)propyl]-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-[1-(4-methoxyphenyl)propyl]acetamide;
2-(2,4-dioxo-1-p-tolyl-1,3-diazaspiro[4.5]dec-3-yl)-N-[1-(2-trifluoromethylphenyl)propyl]acetamide;
2-(2,4-dioxo-1-p-tolyl-1,3-diazaspiro[4.5]dec-3-yl)-N-[1-(3-trifluoromethylphenyl)propyl]acetamide;
2-(2,4-dioxo-1-p-tolyl-1,3-diazaspiro[4.5]dec-3-yl)-N-(1-phenylbutyl)acetamide;
2-(2,4-dioxo-1-p-tolyl-1,3-diazaspiro[4.5]dec-3-yl)-N-(2-methyl-1-phenylpropyl)acetamide;
N-[1-(3-chlorophenyl)propyl]-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-[1-(2-ethoxyphenyl)propyl]acetamide;
2-(2,4-dioxo-1-p-tolyl-1,3-diazaspiro[4.5]dec-3-yl)-N-[1-(2-isopropoxyphenyl)propyl]acetamide;
2-(2,4-dioxo-1-p-tolyl-1,3-diazaspiro[4.5]dec-3-yl)-N-[1-(3-methoxyphenyl)propyl]acetamide;
N-[1-(3-methoxyphenyl)propyl]-2-[1-(6-methylpyridin-3-yl)-2,4-dioxo-1,3-diazaspiro[4.5]dec-3-yl]acetamide;
N-[1-(3-methoxyphenyl)butyl]-2-[1-(6-methylpyridin-3-yl)-2,4-dioxo-1,3-diazaspiro[4.5]dec-3-yl]acetamide;
2-[4,4-diethyl-3-(6-methylpyridin-3-yl)-2,5-dioxoimidazolidin-1-yl]-N-[1-(3-methoxyphenyl)butyl]-acetamide;
2-(4,4-diethyl-2,5-dioxo-3-p-tolylimidazolidin-1-yl)-N-[1-(3-methoxyphenyl)butyl]acetamide;
2-[4,4-diethyl-3-(4-hydroxymethylphenyl)-2,5-dioxo-imidazolidin-1-yl]-N-[1-(3-methoxyphenyl)butyl]-acetamide;
N-[1-(3-chlorophenyl)butyl]-2-[4,4-diethyl-3-(4-hydroxymethylphenyl)-2,5-dioxoimidazolidin-1-yl]-acetamide;
N-[1-(3-chlorophenyl)butyl]-2-[1-(4-hydroxymethyl-phenyl)-2,4-dioxo-1,3-diazaspiro[4.5]dec-3-yl]-acetamide;
2-(2,4-dioxo-1-p-tolyl-1,3-diazaspiro[4.5]dec-3-yl)-N-[1-(3-methoxyphenyl)butyl]acetamide.

A subject of the invention is also a process for preparing the compounds of general formula (I).

In accordance with the invention, the compounds of formula (I) may be prepared according to the general process described in Scheme 1 below.

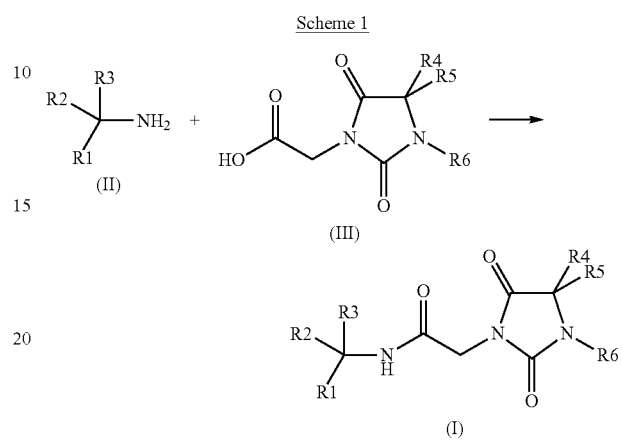

The compounds of formula (I) in which $R_1$, $R_2$, $R_3$, $R_4$, $R_5$ and $R_6$ are as defined above may be prepared by reaction between the amines of formula (II) and the carboxylic acids of formula (III) activated via one of the methods well known to those skilled in the art according to Scheme 1, for example using the coupling reagent TBTU (2-(1H-benzotriazol-1-yl)-1,1,3,3-tetramethyluronium tetrafluoroborate) as described in Boomqaarden, Monika et al. *Pharmazie* 1992, (710). The amines of general formula (II) in which $R_1$, $R_2$ and $R_3$ are as defined above for the compounds of formula (I) are commercial compounds or prepared according to techniques that are well known to those skilled in the art, such as Pohland A. et al., J. Am. Chem. Soc., 1953, 5898-5899.

Synthesis of the Intermediates (III)

The carboxylic acids of general formula (III), in which $R_4$, $R_5$ and $R_6$ are as defined above for the compounds of formula (I), may be prepared according to Scheme 2 below:

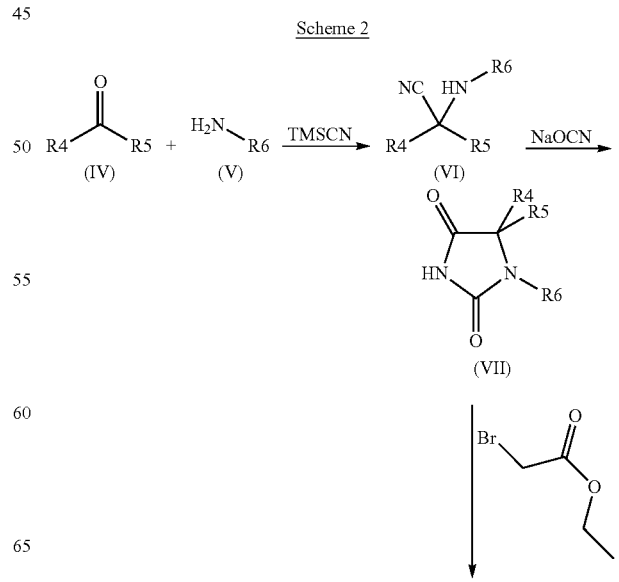

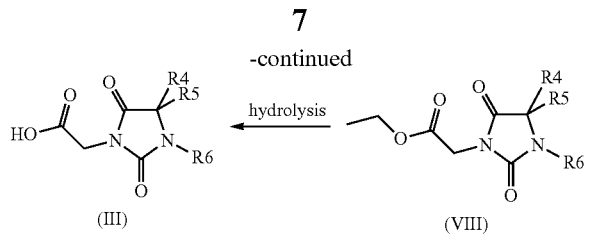

The nitrile compounds of formula (VI) are obtained from the ketones of formula (IV) reacted with the amines of formula (V) in the presence of trimethylsilyl cyanide, in accordance, for example, with the conditions described in Matsumoto K. et al., *Helv. Chim. Acta* 2005, 88 (7), 1734-1753 or Nieto M. J. et al., *J. Comb. Chem.* 2005, 7 (2), 258-263.

The dioxo-imidazolidine intermediates of formula (VII) may be prepared by reacting the nitrile derivatives (VI) with sodium isocyanate, followed by work-up in acidic medium according, for example, to the conditions described in patent DE 1 032 258.

The esters of formula (VIII) are obtained by alkylation of the dioxo-imidazolidine intermediates of formula (VII) using ethyl bromoacetate according to the methods that are well known to those skilled in the art.

The carboxylic acids of formula (III) may be prepared by hydrolysis in basic medium of the esters of formula (VIII) according to the methods that are well known to those skilled in the art.

The functional groups that may be present in the reaction intermediates used in the process may be protected, either permanently or temporarily, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", published by McOmie J. W. F., Plenum Press, 1973, in "Protective Groups in Organic Synthesis", 2nd edition, Greene T. W. and Wuts P. G. M., published by John Wiley & Sons, 1991, and in "Protecting Groups", Kocienski P. J., 1994, Georg Thieme Verlag.

The compounds (I) according to the invention, and also the pharmaceutically acceptable salts, solvates and/or hydrates thereof, have inhibitory properties on the enzyme SOAT-1. This inhibitory activity on the enzyme SOAT-1 is measured according to a HepG2 primary enzymatic test, as described in Example 23. The preferred compounds of the present invention have a concentration that enables inhibition of 50% of the response of the enzyme ($IC_{50}$) of less than or equal to 1000 nM, preferentially less than or equal to 300 nM and advantageously less than or equal to 50 nM.

A subject of the present invention is also, as medicaments, the compounds of formula (I) as described above, and also the pharmaceutically acceptable salts and pharmaceutically acceptable solvates and/or hydrates thereof.

A subject of the present invention is the use of at least one compound of formula (I), or pharmaceutically acceptable salts or solvates and/or hydrates thereof, for the manufacture of a medicament for preventing and/or treating sebaceous gland disorders such as hyperseborrhoea, acne, seborrhoeic dermatitis or atopic dermatitis, ocular pathologies such as blepharitis or meibomitis (disorder of the Meibomian gland) or pathologies such as hypercholesterolaemia, arteriosclerosis (or atherosclerosis) or Alzheimer's disease. The compounds according to the invention are particularly suitable for the manufacture of a pharmaceutical composition for treating acne. The compounds according to the invention are thus suitable for use in the pathologies listed above.

A subject of the present invention is also a pharmaceutical or cosmetic composition comprising, in a physiologically acceptable support, at least one compound of formula (I) as defined above, or a pharmaceutically acceptable salt or solvate and/or hydrate thereof. The compositions according to the invention thus comprise a physiologically acceptable support or at least one physiologically or pharmaceutically acceptable excipient, chosen according to the desired cosmetic or pharmaceutical form and the chosen mode of administration.

The term "physiologically acceptable support or medium" means a support that is compatible with the skin, mucous membranes and/or the integuments.

The administration of the composition according to the invention may be performed via the enteral, parenteral, rectal, topical or ocular route. Preferably, the pharmaceutical composition is conditioned in a form that is suitable for topical application.

Via the enteral route, the composition, more particularly the pharmaceutical composition, may be in the form of tablets, gel capsules, coated tablets, syrups, suspensions, solutions, powders, granules, emulsions, microspheres or nanospheres or lipid or polymer vesicles allowing controlled release. Via the parenteral route, the composition may be in the form of solutions or suspensions for perfusion or for injection.

The compositions according to the invention contain a compound according to the invention, in an amount sufficient to obtain the desired therapeutic, prophylactic or cosmetic effect. The compounds according to the invention are generally administered at a daily dose of about 0.001 mg/kg to 100 mg/kg of body weight, in 1 to 3 dosage intakes. The compounds are used systemically at a concentration generally of between 0.001% and 10% by weight and preferably between 0.01% and 5% by weight relative to the weight of the composition.

Via the topical route, the pharmaceutical composition according to the invention is more particularly intended for treating the skin and mucous membranes and may be in the form of ointments, creams, milks, pomades, powders, impregnated pads, syndets, solutions, gels, sprays, mousses, suspensions, lotions, sticks, shampoos or washing bases. It may also be in the form of suspensions of microspheres or nanospheres or lipid or polymer vesicles or polymer patches and hydrogels allowing controlled release. This topical composition may be in anhydrous form, in aqueous form or in the form of an emulsion.

The compounds are used topically at a concentration generally of between 0.001% and 10% by weight and preferably between 0.01% and 5% by weight relative to the total weight of the composition.

The compounds of formula (I) according to the invention and the pharmaceutically acceptable salts or solvates and/or hydrates thereof also find an application in the cosmetics field, in particular in body and hair hygiene and more particularly for combating or preventing greasy skin or hair or a greasy scalp.

A subject of the invention is thus also the cosmetic use of a composition comprising, in a physiologically acceptable support, at least one of the compounds of formula (I), optionally in the form of a pharmaceutically acceptable salt or solvate and/or hydrate, for body or hair hygiene.

The cosmetic composition according to the invention containing, in a cosmetically acceptable support, at least one compound of formula (I) or a pharmaceutically acceptable salt or solvate and/or hydrate thereof may especially be in the form of a cream, a milk, a lotion, a gel, an ointment, a pomade, a suspension of microspheres or nanospheres or lipid or polymer vesicles, impregnated pads, solutions, sprays, mousses, sticks, soaps, shampoos or washing bases.

The pharmaceutical and cosmetic compositions as described previously may also contain inert or even pharmacodynamically active additives as regards the pharmaceutical compositions, or combinations of these additives, and especially:

wetting agents;
flavour enhancers;
preserving agents such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol or certain metal-chelating agents;
emollients;
moisturizers, for instance glycerol, PEG-400, thiamorpholinone and derivatives thereof, or urea;
carotenoids and especially β-carotene;
α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and salts, amides or esters thereof.

Needless to say, a person skilled in the art will take care to select the optional compound(s) to be added to these compositions such that the advantageous properties intrinsically associated with the present invention are not, or are not substantially, adversely affected by the envisaged addition. Moreover, in general, the same preferences as those indicated previously for the compounds of formula (I) apply mutatis mutandis to the medicaments and cosmetic and pharmaceutical compositions and to the use using the compounds of the invention.

The preparation of the active compounds of formula (I) according to the invention, and the results of the biological activity of such compounds, are given hereinbelow as illustrations and with no limiting nature.

PROCEDURES

Example 1

2-(2,4-Dioxo-1-p-tolyl-1,3-diaza-spiro[4.5]dec-3-yl)-N-(1-phenylbutyl)acetamide

Step 1.1 1-p-Tolylaminocyclohexanecarbonitrile 10 g of cyclohexanone (101.9 mmol, 1 eq.) (starting material 1) are dissolved in 150 ml of acetic acid (15 vol.) in a 500 ml three-necked flask, at room temperature and under nitrogen, the mixture is cooled in an ice bath (10° C.) and followed by portionwise addition of 13.1 g of para-toluidine (starting material 2) (122.3 mmol, 1.2 eq.), and the mixture is then stirred for 15 minutes at 10° C. 15 ml (112.1 mmol, 1.1 eq.) of trimethylsilyl cyanide are then introduced. The reaction medium is stirred overnight at room temperature. It is then poured gently into ice-cold 20% ammonium hydroxide solution (300 ml) until the pH is basic, and extracted with 300 ml of dichloromethane. The aqueous phase is again extracted with 200 ml of dichloromethane. The organic phases are combined and washed with 400 ml of water and then dried over magnesium sulfate. After evaporation, the residue is triturated in heptane, and the product 1-p-tolylaminocyclohexanecarbonitrile is isolated in the form of a white solid.

Step 1.2
1-p-Tolyl-1,3-diazaspiro[4.5]decane-2,4-dione 18 g of 1-p-tolylaminocyclohexanecarbonitrile are dissolved in 90 ml of acetic acid in a 250 ml three-necked flask, at room temperature and under nitrogen, the mixture is heated to 35° C., 8.74 g of NaOCN are then added portionwise, heating is continued up to 60° C. and the mixture is stirred for 2 hours. 29 ml of 12N HCl and then 19 ml of water are introduced into the reaction medium, which is then heated for 30 minutes from 50 to 90° C. The reaction medium is transferred into about 1 l of water and a white precipitate forms, which is recovered by filtration and then dried. The product 1-p-tolyl-1,3-diazaspiro[4.5]decane-2,4-dione is obtained in the form of a white solid.

Step 1.3 (2,4-Dioxo-1-p-tolyl-1,3-diaza-spiro[4.5]dec-3-yl)acetic acid ethyl ester 17.9 g (0.130 mol; 1.1 eq.) of potassium carbonate are added to a solution of 30.4 g (0.117 mol; 1 eq.) of 1-p-tolyl-1,3-diazaspiro[4.5]decane-2,4-dione in 150 ml of DMF, and 16 ml (0.141 mol; 1.2 eq.) of ethyl bromoacetate are then added dropwise to the reaction medium. The cream-coloured reaction medium suspension is stirred at room temperature for 18 hours. The reaction medium is poured into 300 ml of water and the white precipitate is filtered off, rinsed with water and then dried in an oven under vacuum at 40° C. for 48 hours. The product (2,4-dioxo-1-p-tolyl-1,3-diaza-spiro[4.5]dec-3-yl)acetic acid ethyl ester is obtained in the form of a white solid.
Melting point=132° C.

Step 1.4 (2,4-Dioxo-1-p-tolyl-1,3-diaza-spiro[4.5]dec-3-yl)acetic acid 172 ml (0.172 mol; 1.5 eq.) of 1N sodium hydroxide are added to a solution of 39.5 g (0.114 mol; 1 eq.) of (2,4-dioxo-1-p-tolyl-1,3-diazaspiro[4.5]dec-3-yl)acetic acid ethyl ester in 400 ml of THF. The reaction medium is stirred at room temperature for about 72 hours. The reaction medium is concentrated and 250 ml of ethyl acetate are added, followed by 400 ml of water. 100 ml of 1N NaOH are added and the aqueous solution is washed with 250 ml of ethyl acetate. The aqueous phase is concentrated and then acidified to pH 4 approximately with 170 ml of 1N acetic acid. The white precipitate is filtered off and then rinsed with water until the pH of the filtrates is approximately equal to 7, and dried in an oven under vacuum at 40° C. The product (2,4-dioxo-1-p-tolyl-1,3-diazaspiro[4.5]dec-3-yl)acetic acid is obtained in the form of a white solid.
Melting point=206° C.

Step 1.5 2-(2,4-Dioxo-1-p-tolyl-1,3-diaza-spiro[4.5]dec-3-yl)-N-(1-phenylbutyl)acetamide 170 µl (0.098 mmol, 0.1 eq.) of N,N-diisopropylethylamine and 204 mg (0.63 mmol, 2 eq.) of TBTU are added to a solution of 100 mg of (2,4-dioxo-1-p-tolyl-1,3-diazaspiro

[4.5]dec-3-yl)acetic acid in 30 ml of NMP. The solution is stirred for 20 minutes, and 70 mg (0.47 mmol, 1.5 eq.) of 1-phenylbutylamine (starting material 3) are added. The reaction medium is stirred overnight at room temperature. It is then poured into 1N hydrochloric acid solution and extracted with ethyl acetate. The organic phase is then washed with water, then with 1N sodium hydroxide solution, and then again with water. It is dried over sodium sulfate. The residue is precipitated from dichloromethane and heptane. 2-(2,4-Dioxo-1-p-tolyl-1,3-diazaspiro[4.5]dec-3-yl)-N-(1-phenylbutyl)acetamide is obtained in the form of a white solid. Melting point=208-210° C.

(DMSO) 0.84-0.88 (t, 3H); 0.90-0.96 (m, 1H); 1.16-1.31 (m, 2H); 1.33-1.44 (m, 2); 1.53 (m, 3H); 1.59-1.70 (m, 2H); 1.82-1.93 (m, 4H); 2.34 (s, 3H); 4.04-4.14 (m, 2H); 4.73-4.78 (m, 1H); 7.09-7.11 (d, 2H, J=8.16 Hz); 7.21-7.34 (m, 7H); 8.56-8.58 (d, 1H, J=8.24 Hz).

Examples 2 to 22

Examples 2 to 22 are described in Table 1 below. The compounds are synthesized according to the above procedures, replacing the starting materials 1, 2 and 3 mentioned in Examples 1, 2 and 4 with the products mentioned in Table 1.

TABLE 1

| Example # | IUPAC name | Starting material 1 | Starting material 2 | Starting material 3 | Melting point ° C. | $^1$H NMR - 400 MHz (s = singlet, d = doublet, t = triplet, m = multiplet, q = quartet, J = coupling constant in Hz) |
|---|---|---|---|---|---|---|
| 1 | N-benzyl-2-(2,4-dioxo-1-p-tolyl-1,3-diazaspiro-[4.5]dec-3-yl)-acetamide | cyclohexanone | para-toluidine | benzylamine | 204-206 | (DMSO) 0.92-0.94 (m, 1H); 1.39-1.46 (m, 2H); 1.55 (m, 3H); 1.84-1.96 (m, 4H); 2.35 (s, 3H); 4.11 (s, 2H); 4.30-4.31 (d, 2H); 7.11-7.13 (d, 2H, J = 8.08 Hz); 7.22-7.34 (m, 7H); 8.64-8.67 (m, 1H) |
| 2 | 2-(2,4-dioxo-1-p-tolyl-1,3-diazaspiro[4.5]dec-3-yl)-N-naphthalen-1-ylmethyl-acetamide | cyclohexanone | para-toluidine | C-naphthalen-1-ylmethyl-amine | 211-213 | (DMSO) 0.85-0.98 (m, 1H); 1.40-1.47 (m, 2H); 1.56 (m, 3H); 1.84-1.97 (m, 4H); 2.35 (s, 3H); 4.12 (s, 2H); 4.76-4.78 (m, 2H); 7.12-7.14 (d, 2H, J = 8.16 Hz); 7.28-7.30 (d, 2H, J = 8.12 Hz); 7.44-7.48 (m, 2H); 7.49-7.58 (m, 2H); 7.85-7.87 (m, 1H); 7.93-7.97 (m, 1H); 8.04-8.06 (m, 1H); 8.70-8.73 (m, 1H) |
| 3 | 2-(2,4-dioxo-1-p-tolyl-1,3-diazaspiro[4.5]dec-3-yl)-N-(3-trifluoromethyl-benzyl)-acetamide | cyclohexanone | para-toluidine | 3-trifluoromethylbenzyl-amine | 196-198 | (DMSO) 0.83-0.97 (m, 1H); 1.39-1.46 (m, 2H); 1.52-1.55 (m, 3H); 1.83-1.96 (m, 4H); 2.32 (s, 3H); 4.13 (s, 2H); 4.40-4.42 (d, 2H); 7.11-7.13 (d, 2H, J = 8.24 Hz); 7.27-7.29 (d, 2H, J = 7.96 Hz); 7.54-7.56 (m, 2H); 7.57-7.63 (m, 2H); 8.76-8.79 (m, 1H) |
| 4 | 2-(2,4-dioxo-1-p-tolyl-1,3-diazaspiro[4.5]dec-3-yl)-N-(1-phenylpropyl)acetamide | cyclohexanone | para-toluidine | 1-phenyl-propylamine | 196-198 | (DMSO) 0.81-0.85 (t, 3H); 0.90-0.96 (m, 1H); 0.38-1.44 (m, 2H); 1.53 (m, 3H); 0.65-1.72 (m, 2H); 1.82-1.93 (m, 4H); 2.34 (s, 3H); 4.05-4.15 (m, 2H); 4.64-4.70 (m, 1H); 7.09-7.11 (d, 2H, J = 8.2 Hz); 7.20-7.37 (m, 7H); 8.55-8.57 (d, 1H, J = 8.28 Hz) |
| 5 | 2-(2,4-dioxo-1-p-tolyl-1,3-diazaspiro[4.5]dec-3-yl)-N-((R)-1-phenylpropyl)-acetamide | cyclohexanone | para-toluidine | (S)-(−)-1-phenylpropyl-amine | 210-212 | (DMSO) 0.81-0.85 (t, 3H); 0.88-0.96 (m, 1H); 1.38-1.44 (m, 2H); 1.53 (m, 3H); 1.65-1.72 (2H); 1.82-1.99 (m, 4H); 2.34 (s, 3H); 4.05-4.15 (m, 2H); 4.64-4.70 (m, 1H); 7.09-7.11 (d, 2H, J = 8.12 Hz); 7.21-7.36 (m, 7H); 8.56-8.58 (d, 1H, J = 8.24 Hz) |
| 6 | 2-(2,4-dioxo-1-p-tolyl-1,3-diazaspiro[4.5]dec-3-yl)-N-((S)-1-phenylpropyl)-acetamide | cyclohexanone | para-toluidine | (R)-(+)-1-phenylpropyl-amine | 210-212 | (DMSO) 0.81-0.85 (t, 3H); 0.90-0.96 (m, 1H); 1.38-1.44 (m, 2H); 1.53 (m, 3H); 1.65-1.72 (m, 2H); 1.82-1.99 (m, 4H); 2.34 (s, 3H); 4.04-4.15 (m, 2H); 4.64-4.70 (m, 1H); 7.09-7.11 (d, 2H, J = 8.16 Hz); 7.21-7.34 (m, 7H); 8.55-8.57 (d, 1H, J = 8.28 Hz) |
| 7 | 2-(2,4-dioxo-1-p-tolyl-1,3-diazaspiro[4.5]dec-3-yl)-N-(1-o-tolyl-propyl)acetamide | cyclohexanone | para-toluidine | 1-o-tolyl-propylamine | — | (CDCl$_3$) 0.8 (t, 3H); 0.9 (m, 1H); 1.44-1.56 (m, 7H); 1.69-2.0 (m, 4H); 2.31 (s, 3H); 2.32 (s, 3H); 4.07-4.17 (dd, 2H); 5.05 (q, 1H); 6.05 (d, 1H); 6.98 (d, 2H); 7.1 (dd, 4H); 7.16-7.19 (m, 2H) |
| 8 | 2-(2,4-dioxo-1-p-tolyl-1,3-diazaspiro[4.5]dec-3-yl)-N-(1-o-tolyl-butyl)acetamide | cyclohexanone | para-toluidine | 1-o-tolyl-butylamine | — | (CDCl$_3$) 0.8 (t, 3H); 0.9 (m, 1H); 1.34-1.43 (m, 2H); 1.52-2.1 (m, 11H); 2.39 (s, 3H); 2.4 (s, 3H); 4.16-4.24 (dd, 2H); 5.22 (q, 1H); 6.14 (d, 1H); 7.06 (d, 2H); 7.16-7.28 (m, 6H) |
| 9 | 2-(2,4-dioxo-1-p-tolyl-1,3-diazaspiro[4.5]dec-3-yl)-N-(2-methyl-1-o-tolylpropyl)-acetamide | cyclohexanone | para-toluidine | 2-methyl-1-o-tolyl-propylamine | — | (CDCl$_3$) 0.6 (d, 3H); 0.65 (t, 1H); 0.86 (d, 3H); 1.13-1.25 (m, 1H); 1.43-1.62 (m, 5H); 1.8-2.0 (m, 4H); 3.06-4.2 (dd, 2H); 4.94 (t, 1H); 6.31 (d, 1H); 6.97 (d, 2H); 7.03-7.12 (m, 2H); 7.17-7.19 (m, 4H) |
| 10 | 2-(2,4-dioxo-1-p-tolyl-1,3-diazaspiro[4.5]dec-3-yl)-N-[1-(2-methoxyphenyl)-butyl]acetamide | cyclohexanone | para-toluidine | 1-(2-methoxy-phenyl)-butylamine | — | (CDCl$_3$) 0.87 (t, 3H); 0.92-1.13 (m, 1H); 1.13-1.35 (m, 2H); 1.52-1.8 (m, 7H); 1.94-2.09 (m, 4H); 2.38 (s, 3H); 3.86 (s, 3H); 4.13-4.23 (dd, 2H); 5.1 (q, 1H); 6.74 (d, 1H); 6.89 (t, 2H); 7.06 (d, 2H); 7.14 (d, 1H); 7.21-7.26 (m, 3H) |

TABLE 1-continued

| Example # | IUPAC name | Starting material 1 | Starting material 2 | Starting material 3 | Melting point °C. | $^1$H NMR - 400 MHz (s = singlet, d = doublet, t = triplet, m = multiplet, q = quartet, J = coupling constant in Hz) |
|---|---|---|---|---|---|---|
| 11 | 2-(2,4-dioxo-1-p-tolyl-1,3-diaza-spiro[4.5]dec-3-yl)-N-[1-(2-fluorophenyl)-propyl]acetamide | cyclohexanone | para-toluidine | 1-(2-fluoro-phenyl)-propylamine | 201-203 | (DMSO) 0.83-0.87 (t, 3H); 0.90-0.93 (m, 1H); 1.38-1.44 (m, 2H); 1.53 (m, 3H); 1.65-1.73 (m, 2H); 1.81-1.92 (m, 4H); 2.34 (s, 3H); 4.06-4.17 (m, 2H); 4.92-4.98 (m, 1H); 7.08-7.11 (d, 2H, J = 8.16 Hz); 7.13-7.20 (m, 2H); 7.26-7.30 (m, 3H); 7.36-7.40 (m, 1H); 8.65-8.67 (d, 1H, J = 8.04 Hz) |
| 12 | N-[1-(2,4-dimethyl-phenyl)propyl]-2-(2,4-dioxo-1-p-tolyl-1,3-diaza-spiro[4.5]dec-3-yl)acetamide | cyclohexanone | para-toluidine | 1-(2,4-dimethyl-phenyl)-propylamine | 179-181 | (DMSO) 0.82-0.86 (t, 3H); 0.90-0.93 (m, 1H); 1.38-1.44 (m, 2H); 1.53 (m, 3H); 1.59-1.66 (m, 2H); 1.81-1.92 (m, 4H); 2.22 (s, 3H); 2.26 (s, 3H); 2.34 (s, 3H); 4.01-4.12 (m, 2H); 4.80-4.85 (m, 1H); 6.94 (s, 1H); 6.97-6.99 (d, 1H, J = 7.84 Hz); 7.08-7.11 (d, 2H, J = 8.16 Hz); 7.15-7.17 (d, 1H, J = 7.84 Hz); 7.26-7.28 (d, 2H, J = 8.12 Hz); 8.49-8.52 (d, 1H, J = 8.08 Hz) |
| 13 | 2-(2,4-dioxo-1-p-tolyl-1,3-diaza-spiro[4.5]dec-3-yl)-N-(1-p-tolyl-propyl)acetamide | cyclohexanone | para-toluidine | 1-p-tolyl-propylamine | 166-168 | (DMSO) 0.79-0.83 (t, 3H); 0.86-0.93 (m, 1H); 1.38-1.44 (m, 2H); 1.53 (m, 3H); 1.62-1.70 (m, 2H); 1.82-1.93 (m, 4H); 2.27 (s, 3H); 2.34 (s, 3H); 4.03-4.13 (m, 2H); 4.59-4.65 (m, 1H); 7.09-7.18 (m, 6H); 7.26-7.28 (d, 2H, J = 8.04 Hz); 8.50-8.52 (d, 1H, J = 8.28 Hz) |
| 14 | N-[1-(4-chloro-phenyl)propyl]-2-(2,4-dioxo-1-p-tolyl-1,3-diaza-spiro[4.5]dec-3-yl)acetamide | cyclohexanone | para-toluidine | 1-(4-chloro-phenyl)-propylamine | 175-177 | (DMSO) 0.81-0.85 (t, 3H); 0.90-0.96 (m, 1H); 1.38-1.44 (m, 2H); 1.54 (m, 3H); 1.63-1.70 (m, 2H); 1.82-1.92 (m, 4H); 2.34 (s, 3H); 4.05-4.15 (m, 2H); 4.63-4.69 (m, 1H); 7.09-7.11 (d, 2H, J = 8.12 Hz); 7.26-7.32 (m, 4H); 7.37-7.39 (d, 2H, J = 8.4 Hz) 8.59-8.61 (d, 1H, J = 8.04 Hz) |
| 15 | 2-(2,4-dioxo-1-p-tolyl-1,3-diaza-spiro[4.5]dec-3-yl)-N-[1-(4-methoxyphenyl)-propyl]acetamide | cyclohexanone | para-toluidine | 1-(4-methoxy-phenyl)-propylamine | 176-178 | (DMSO) 0.79-0.82 (t, 3H); 0.84-0.96 (m, 1H); 1.39-1.45 (m, 2H); 1.54 (m, 3H); 1.62-1.69 (m, 2H); 1.82-1.93 (m, 4H); 2.34 (s, 3H); 3.72 (s, 3H); 4.02-4.13 (m, 2H); 4.58-4.64 (m, 1H); 6.87-6.89 (d, 2H, J = 8.64 Hz); 7.09-7.11 (d, 2H, J = 8.12 Hz); 7.19-7.21 (d, 2H, J = 8.6 Hz); 7.26-7.28 (d, 2H, J = 8.04 Hz); 8.48-8.50 (d, 1H, J = 8.2 Hz) |
| 16 | 2-(2,4-dioxo-1-p-tolyl-1,3-diaza-spiro[4.5]dec-3-yl)-N-[1-(2-trifluoromethyl-phenyl)propyl]-acetamide | cyclohexanone | para-toluidine | 1-[2-(trifluoromethyl)-phenylpropyl-amine | 180-182 | (DMSO) 0.88-0.92 (t, 3H); 1.37-1.42 (m, 2H); 1.44-1.53 (m, 3H); 1.60-1.67 (m, 2H); 1.81-1.92 (m, 4H); 2.34 (s, 3H); 4.06-4.16 (m, 2H); 5.01-5.06 (m, 1H); 7.09-7.11 (d, 2H, J = 8.2 Hz); 7.26-7.28 (d, 2H, J = 8 Hz); 7.44-7.48 (m, 1H); 7.65-7.72 (m, 3H); 8.72-8.74 (d, 1H, J = 7.88 Hz) |
| 17 | 2-(2,4-dioxo-1-p-tolyl-1,3-diaza-spiro[4.5]dec-3-yl)-N-[1-(3-trifluoromethyl-phenyl)propyl]-acetamide | cyclohexanone | para-toluidine | 1-[3-(trifluoromethyl)-phenylpropyl-amine | 197-199 | (DMSO) 0.83-0.87 (t, 3H); 0.90-0.93 (m, 1H); 1.38-1.41 (m, 2H); 1.44-1.53 (m, 3H); 1.67-1.74 (m, 2H); 1.81-1.92 (m, 4H); 2.34 (s, 3H); 4.08-4.18 (m, 2H); 4.75-4.81 (m, 1H); 7.08-7.10 (d, 2H, J = 8.16 Hz); 7.26-7.28 (d, 2H, J = 8.08 Hz); 7.55-7.65 (m, 4H); 8.69-8.71 (d, 1H, J = 8.08 Hz) |
| 18 | 2-(2,4-dioxo-1-p-tolyl-1,3-diaza-spiro[4.5]dec-3-yl)-N-(1-phenyl-butyl)acetamide | cyclohexanone | para-toluidine | 1-phenyl-butylamine | 208-210 | (DMSO) 0.84-0.88 (t, 3H); 0.90-0.96 (m, 1H); 1.16-1.31 (m, 2H); 1.33-1.44 (m, 2); 1.53 (m, 3H); 1.59-1.70 (m, 2H); 1.82-1.93 (m, 4H); 2.34 (s, 3H); 4.04-4.14 (m, 2H); 4.73-4.78 (m, 1H); 7.09-7.11 (d, 2H, J = 8.16 Hz); 7.21-7.34 (m, 7H); 8.56-8.58 (d, 1H, J = 8.24 Hz) |
| 19 | 2-(2,4-dioxo-1-p-tolyl-1,3-diaza-spiro[4.5]dec-3-yl)-N-(2-methyl-1-phenylpropyl)-acetamide | cyclohexanone | para-toluidine | 2-methyl-1-phenyl-propylamine | 198-200 | (DMSO) 0.71-0.73 (d, 3H); 0.88-0.89 (d, 3H); 0.92-0.96 (m, 1H); 1.38-1.44 (m, 2H); 1.53 (m, 3H); 1.81-1.98 (m, 5H); 2.34 (s, 3H); 4.06-4.17 (m, 2H); 4.53-4.57 (m, 1H); 7.08-7.10 (d, 3H); 7.21-7.34 (m, 6H); 8.52-8.55 (d, 1H, J = 8.92 Hz) |
| 20 | N-[1-(3-chloro-phenyl)propyl]-2-(2,4-dioxo-1-p-tolyl-1,3-diaza-spiro[4.5]dec-3-yl)acetamide | cyclohexanone | para-toluidine | 1-(3-chloro-phenyl)-propylamine | 191-193 | (DMSO) 0.81-0.85 (t, 3H); 0.90-0.93 (m, 1H); 1.38-1.44 (m, 2H); 1.53 (m, 3H); 1.64-1.71 (m, 2H); 1.82-1.93 (m, 4H); 2.34 (s, 3H); 4.07-4.12 (m, 2H); 4.65-4.71 (m, 1H); 7.09-7.11 (d, 2H, J = 8.16 Hz); 7.25-7.30 (m, 4H); 7.34-7.38 (m, 2H); 8.60-8.62 (d, 1H, J = 8.04 Hz). |

TABLE 1-continued

| Example # | IUPAC name | Starting material 1 | Starting material 2 | Starting material 3 | Melting point °C. | $^1$H NMR - 400 MHz (s = singlet, d = doublet, t = triplet, m = multiplet, q = quartet, J = coupling constant in Hz) |
|---|---|---|---|---|---|---|
| 21 | 2-(2,4-dioxo-1-p-tolyl-1,3-diaza-spiro[4.5]dec-3-yl)-N-[1-(2-ethoxyphenyl)-propyl]acetamide | cyclohexanone | para-toluidine | 1-(2-ethoxy-phenyl)propylamine | 187-189 | (DMSO) 0.82-0.86 (t, 3H); 0.90-0.96 (m, 1H); 1.29-1.34 (t, 3H); 1.36-1.45 (m, 2H); 1.53-1.59 (m, 4H); 1.53-1.72 (m, 1H); 1.82-1.93 (m, 4H); 2.34 (s, 3H); 4.01-4.17 (m, 4H); 5.04-5.10 (m, 1H); 6.88-6.95 (m, 2H); 7.08-7.10 (d, 2H, J = 8.2 Hz); 7.16-7.28 (m, 4H); 8.42-8.44 (d, 1H, J = 8.52 Hz), |
| 22 | 2-(2,4-dioxo-1-p-tolyl-1,3-diaza-spiro[4.5]dec-3-yl)-N-[1-(2-isopropoxy-phenyl)propyl]-acetamide | cyclohexanone | para-toluidine | 1-(2-isopropoxyphenyl)-propylamine | 152-154 | (DMSO) 0.82-0.86 (t, 3H); 0.90-0.96 (m, 1H); 1.27-1.31 (d, 6H); 1.38-1.42 (m, 2H); 1.45-1.57 (m, 4H); 1.63-1.70 (m, 1H); 1.82-1.93 (m, 4H); 2.34 (s, 3H); 4.07-4.17 (m, 2H); 4.59-4.63 (m, 1H); 5.01-5.07 (m, 1H); 6.86-6.89 (t, 1H); 6.95-6.97 (d, 1H, J = 8.12 Hz); 7.09-7.11 (d, 2H, J = 8.16 Hz); 7.15-7.17 (t, 1H); 7.19-7.28 (m, 3H); 8.38-8.40 (d, 1H, J = 8.52 Hz). |

All the NMR (nuclear magnetic resonance) spectra are in accordance with the proposed structures. The chemical shifts are expressed in parts per million. The internal reference is tetramethylsilane. The following abbreviations are used: CDCl$_3$=deuterated chloroform, DMSO=deuterated dimethyl sulfoxide Example 23

Biological Tests

The compounds of formula (I) according to the invention were subjected to a test for evaluating their inhibitory activity towards the enzyme ACAT-1, inspired by the following publication: "Identification of ACAT1- and ACAT2-specific inhibitors using a novel, cell based fluorescence assay: individual ACAT uniqueness", J. Lipid. Res. (2004) vol. 45, pages 378-386.

The principle of this test is based on the use of NBD-cholesterol, a cholesterol analogue whose fluorescence depends on its environment. When this molecule is in a polar environment, it is weakly fluorescent, whereas in a non-polar environment, it is strongly fluorescent. Free NBD-cholesterol becomes inserted in cell membranes and is weakly fluorescent in this polar environment. When NBD-cholesterol is esterified with ACAT, the NBD-cholesterol ester enters non-polar lipid droplets and is then strongly fluorescent.

The method below is applied: HepG2 cells are incubated in the presence of NBD-cholesterol (1 μg/ml) and of the test compound of formula (I) in black 96-well transparent-bottomed plates, at a rate of 30 000 cells per well. After incubation for 6 hours at 37° C. under 5% CO$_2$, the medium is removed by turning upside-down and the cells are washed with twice 100 μl of PBS. After addition of 50 μl of lysis buffer (10 mM NaPO$_4$, 1% Igepal), the plates are shaken for 5 minutes and the fluorescence is read (excitation at 490 nm, emission at 540 nm) on a Fusion machine (Perkin-Elmer). By way of illustration, an IC$_{50}$ of 1187 nM is obtained for compound (I), an IC$_{50}$ of 50 nM is obtained for compound (4), an IC$_{50}$ of 36 nM is obtained for compound (6), an IC$_{50}$ of 31 nM is obtained for compound (8), an IC$_{50}$ of 100 nM is obtained for compound (9), an IC$_{50}$ of 60 nM is obtained for compound (13), an IC$_{50}$ of 9 nM is obtained for compound (17) and an IC$_{50}$ of 23 nM is obtained for compound (19).

Example 24

Formulations

Various formulations containing the compounds according to the invention are given below.

A - ORAL ROUTE (a) 0.2 g tablet

| | |
|---|---|
| Compound 12 | 0.01 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml vials

| | |
|---|---|
| Compound 1 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavouring | qs |
| Purified water | qs 5 ml |

B - TOPICAL ROUTE (a) Ointment

| | |
|---|---|
| Compound 5 | 0.300 g |
| White petroleum jelly codex | qs 100 g |

(d) Lotion

| | |
|---|---|
| Compound 9 | 0.100 g |
| Polyethylene glycol (PEG 400) | 69.900 g |
| 95% Ethanol | 30.000 g |

(e) Hydrophobic ointment

| | |
|---|---|
| Compound 11 | 0.300 g |
| Isopropyl myristate | 36.400 g |
| Silicone oil (Rhodorsil 47 V 300) | 36.400 g |
| Beeswax | 13.600 g |
| Silicone oil (Abil 300 000 cSt) | qs 100 g |

(f) Nonionic oil-in-water cream

| | |
|---|---|
| Compound 3 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

The invention claimed is:
1. A compound of formula (I):

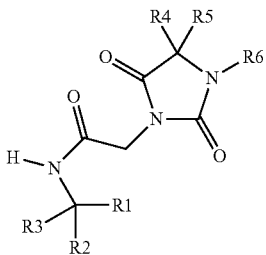

in which:
R$_1$ and R$_6$ represent identical or different groups chosen from the following groups:
    phenyl group or naphthyl group, optionally substituted with one to three identical or different groups R$_a$, and
    heteroaryl containing either a) from 1 to 4 nitrogen atoms or b) an oxygen or sulfur atom and 1 or 2 nitrogen atoms, optionally substituted with one to three identical or different groups R$_a$,
R$_2$, R$_3$, R$_4$ and R$_5$ are identical or different and represent:
    either a hydrogen atom,
    or a group C$_{1-6}$ alkyl, optionally substituted with one to three groups R$_a$,
    or a group C$_{3-7}$ cycloalkyl, C$_{1-6}$ fluoroalkyl, C$_{1-6}$ fluoroalkyloxy or a group —(CH$_2$)$_n$—C$_{3-7}$ cycloalkyl,
    optionally, the groups R$_2$ and R$_3$ can form with the carbon atom that bears them a group C$_{3-7}$ cycloalkyl or a heterocycle, and
    optionally, the groups R$_4$ and R$_5$ can form with the carbon atom that bears them a group C$_{3-7}$ cycloalkyl or a heterocycle,
R$_a$ represents:
    either a hydrogen, fluorine, chlorine or bromine atom,
    or a group C$_{1-6}$ alkyl, C$_{3-7}$ cycloalkyl, C$_{1-6}$ alkyloxy, C$_{1-6}$ alkylthio, C$_{1-6}$ fluoroalkyl, or C$_{1-6}$ fluoroalkyloxy,
    or a group —(CH$_2$)$_n$—C$_{3-7}$ cycloalkyl, OH, CH$_2$OH, COOR$_b$ or CN,
R$_b$ represents a group C$_{1-6}$ alkyl, C$_{3-7}$ cycloalkyl or —(CH$_2$)$_n$—C$_{3-7}$ cycloalkyl, and
n is an integer equal to 1, 2 or 3,
and also pharmaceutically acceptable salts, solvates or hydrates thereof and conformers or rotamers thereof.

2. The compound according to claim 1, wherein:
R$_2$ represents a hydrogen atom or a group C$_{1-6}$ alkyl, C$_{3-7}$ cycloalkyl, C$_{1-6}$ fluoroalkyl or C$_{1-6}$ fluoroalkyloxy, or
optionally, R$_2$ represents a hydrogen atom or a methyl, ethyl, isopropyl, propyl, cyclopropyl, CH$_2$-cyclopropyl or trifluoromethyl group; and R$_3$ represents a methyl, ethyl, isopropyl, propyl, tert-butyl, cyclopropyl, CH$_2$-cyclopropyl or trifluoromethyl group, or
optionally, R$_2$ represents a hydrogen atom; and R$_3$ represents a methyl, ethyl, isopropyl, propyl, tert-butyl, cyclopropyl, CH$_2$-cyclopropyl or trifluoromethyl group.

3. The compound according to claim 1, wherein:
the groups R$_4$ and R$_5$ form with the carbon atom that bears them a group C$_{3-7}$ cycloalkyl or a heterocycle.

4. The compound according to claim 1, wherein the groups R$_4$ and R$_5$:
individually represent an identical or different group C$_{1-6}$ alkyl, or
can form with the carbon atom that bears them a group C$_{3-7}$ cycloalkyl, optionally substituted with either one or two fluorine atoms or an OH group, or
can form with the carbon atom that bears them a heterocycle.

5. The compound according to claim 4, wherein R$_4$ and R$_5$ represent:
either a methyl, ethyl or propyl group, or
can form with the carbon atom that bears them a cyclopentyl, cyclohexyl or tetrahydropyran-4-yl group.

6. The compound according to claim 1, wherein the group R$_1$ represents a phenyl group or naphthyl group, optionally substituted with one to three identical or different groups R$_a$ selected from the group consisting of methyl, ethyl, propyl, isopropyl, cyclopropyl, CH$_2$-cyclopropyl, methoxy, ethoxy, propyloxy, isopropyloxy, fluoro, chloro, bromo, cyano, trifluoromethyl and trifluoromethyloxy groups.

7. The compound according to claim 6, wherein R$_1$ represents a phenyl group.

8. The compound according to claim 7, wherein one of the substituents R$_a$ is located in a meta position.

9. The compound according to claim 1, wherein R$_6$ Represents a phenyl, pyridyl, pyrazinyl, pyrimidinyl, pyridazinyl, triazinyl, pyrazolyl, isoxazolyl, oxadiazolyl, thiazolyl, thiadiazolyl or triazolyl group, optionally substituted with a group R$_a$.

10. The compound according to claim 9, wherein R$_6$ represents a phenyl group, optionally substituted with one or more groups selected from the group consisting of methyl, trifluoromethyl, fluoro, chloro, methoxy and CH$_2$—OH.

11. The compound according to claim 1, selected from the group consisting of compounds below, and pharmaceutically acceptable salts, solvates, hydrates, conformers and rotamers thereof:
N-benzyl-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-naphthalen-1-ylmethylacetamide;
2-(2,4-dioxo-1-p-tolyl-1 ,3-diazaspiro[4.5]dec-3-yl)-N-(3-trifluoromethyl-benzyl)acetamide;
2-(2,4-dioxo-1-p-tolyl-1,3-diazaspiro[4.5]dec-3-yl)-N-(1-phenylpropyl)acetamide;
2-(2,4-dioxo-1-p-tolyl-1,3-diazaspiro[4.5]dec-3-yl)-N-((R)-1-phenylpropyl)acetamide;
2-(2,4-dioxo-1-p-tolyl-1,3-diazaspiro[4.5]dec-3-yl)-N-((S)-1-phenylpropyl)acetamide;
2-(2,4-dioxo-1-p-tolyl-1,3-diazaspiro[4.5]dec-3-yl)-N-(1-o-tolylpropyl)acetamide;
2-(2,4-dioxo-1-p-tolyl-1,3-diazaspiro[4.5]dec-3-yl)-N-(1-o-tolylbutypacetamide;
2-(2,4-dioxo-1-p-tolyl-1 ,3-diazaspiro[4.5]dec-3-yl)-N-(2-methyl-1-o-tolylpropyl)acetamide;
2-(2,4-dioxo-1-p-tolyl-1 ,3-diazaspiro[4.5]dec-3-yl)-N-[1-(2-methoxyphenyl)butyl]acetamide;
2-(2,4-dioxo-1-p-tolyl-1 ,3-diazaspiro[4.5]dec-3-yl)-N-[1-(2-fluorophenyl)propyl]acetamide;
N-[1-(2,4-dimethylphenyl)propyl]-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-(1-p-tolylpropyl)acetamide;
N-[1-(4-chlorophenyl)propyl]-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-[1-(4-methoxyphenyl)propyl]acetamide;
2-(2,4-dioxo-1-p-tolyl-1,3-diazaspiro[4.5]dec-3-yl)-N-[1-(2-trifluoromethylphenyl)propyl]acetamide;

2-(2,4-dioxo-1-p-tolyl-1,3-diazaspiro[4.5]dec-3-yl)-N-[1-(3-trifluoromethylphenyl)propyl]acetamide;
2-(2,4-dioxo-1-p-tolyl-1,3-diazaspiro[4.5]dec-3-yl)-N-(1-phenylbutyl)acetamide;
2-(2,4-dioxo-1-p-tolyl-1,3-diazaspiro[4.5]dec-3-yl)-N-(2-methyl-1-phenylpropyl)acetamide;
N-[1-(3-chlorophenyl)propyl]-2-(2,4-dioxo-1-p-tolyl-1,3-diazaspiro[4.5]dec-3-yl)acetamide;
2-(2,4-dioxo-1-p-tolyl-1,3-diazaspiro[4.5]dec-3-yl)-N-[1-(2-ethoxyphenyl)propyl]acetamide;
2-(2,4-dioxo-1-p-tolyl-1,3-diazaspiro[4.5]dec-3-yl)-N-[1-(2-isopropoxyphenyl)propyl]acetamide;
2-(2,4-dioxo-1-p-tolyl-1,3-diazaspiro[4.5]dec-3-yl)-N-[1-(3-methoxyphenyl)propyl]acetamide;
N-[1-(3-methoxyphenyl)propyl]-2-[1-(6-methylpyridin-3-yl)-2,4-dioxo-1,3-diazaspiro[4.5]dec-3-yl]acetamide;
N-[1-(3-methoxyphenyl)butyl]-2-[1-(6-methylpyridin-3-yl)-2,4-dioxo-1,3-diazaspiro[4.5]dec-3-yl]acetamide;
2-[4,4-diethyl-3-(6-methylpyridin-3-yl)-2,5-dioxoimidazolidin-1-yl]-N-[1-(3-methoxyphenyl)butyl]acetamide;
2-(4,4-diethyl-2,5-dioxo-3-p-tolylimidazolidin-1-yl)-N-[1-(3-methoxyphenyl)butyl]acetamide;
2-[4,4-diethyl-3-(4-hydroxymethylphenyl)-2,5-dioxoimidazolidin-1-yl]-N-[1-(3-methoxyphenyl)butyl]acetamide;
N-[1-(3-chlorophenyl)butyl]-2-[4,4-diethyl-3-(4-hydroxymethylphenyl)-2,5-dioxoimidazolidin-1-yl]acetamide;
N-[1-(3-chlorophenyl)butyl]-2-[1-(4-hydroxymethylphenyl)-2,4-dioxo-1,3-diazaspiro[4.5]dec-3-yl]acetamide; and
2-(2,4-dioxo-1-p-tolyl-1,3-diazaspiro[4.5]dec-3-yl)-N-[1-(3-methoxyphenyl)butyl]acetamide.

12. A pharmaceutical composition comprising at least one compound according to claim 1 and a pharmaceutically or physiologically acceptable excipient.

13. A pharmaceutical composition comprising, in a physiologically acceptable support, at least one compound according to claim 1.

14. The composition according to claim 13, wherein the concentration of compound(s) according to claim 1 is between 0.001% and 10% by weight relative to the total weight of the composition.

15. The composition according to claim 13, wherein the concentration of compound(s) according to claim 1 is between 0.01% and 5% by weight relative to the total weight of the composition.

16. A cosmetic composition comprising, in a physiologically acceptable support, at least one compound according to claim 1.

17. The composition according to claim 13, wherein the composition is in a form suitable for topical application.

18. The composition according to claim 17, wherein the composition is in the form of a cream, a milk, a lotion, a gel, an ointment, a pomade, a suspension of microspheres or nanospheres or lipid or polymer vesicles, an impregnated pad, a solution, a spray, a mousse, a stick, a soap, a shampoo or a washing base.

19. A cosmetic method, the method comprising administering a composition according to claim 16, to an individual subject in need, for body or hair hygiene.

20. A method of treating a sebaceous gland disorder, an ocular pathology, hypercholesterolaemia or arteriosclerosis comprising administering an effective amount of a pharmaceutical composition according to claim 12, to a subject in need thereof.

21. A method of treating acne comprising administering an effective amount of a pharmaceutical composition according to claim 12, to a subject in need thereof.

22. The method according to claim 20, wherein the ocular pathology is blepharitis or meibomitos.

23. The method according to claim 17, wherein the sebaceous gland disorder is hyperseborrhoea, acne, sebhorrhoeic dermatitis or atopic dermatitis.

24. A method of inhibiting esterification of cholesterol in a subject comprising administering the pharmaceutical composition according to claim 12, to a subject in need thereof.

25. A method of inhibiting SOAT-1 activity in a cell comprising contacting the cell with the pharmaceutical composition according to claim 12.

26. The method according to claim 25, wherein the cell is in a subject in need of SOAT-1 activity being inhibited.

27. A method according to claim 26, wherein the SOAT-1 activity being inhibited is esterification of cholesterol.

28. The compound according to claim 1, wherein the heterocycle formed from $R_2$ and $R_3$ with the carbon atom is:
tetrahydropyran-4-yl, tetrahydrothiopyran-4-yl, tetrahydro-1-oxythiopyran-4-yl or tetrahydro-1,1-dioxythiopyran-4-yl,
piperidine, optionally substituted on the nitrogen atom with a group $C_{1-6}$ alkyl, or
azepan, optionally substituted on the nitrogen atom with a group $C_{1-6}$ alkyl.

29. The compound according to claim 1, wherein the heterocycle formed from $R_4$ and $R_5$ with the carbon atom is:
tetrahydropyran-4-yl, tetrahydrothiopyran-4-yl, tetrahydro-1-oxythiopyran-4-yl or tetrahydro-1,1-dioxythiopyran-4-yl,
piperidine, optionally substituted on the nitrogen atom with a group $C_{1-6}$ alkyl; or
azepan, optionally substituted on the nitrogen atom with a group $C_{1-6}$ alkyl.

30. The compound according to claim 4, wherein the heterocyle is:
tetrahydropyran-4-yl,
tetrahydrothiopyran-4-yl, or
piperidine-4, optionally substituted with a group $C_{1-6}$ alkyl or $C_{3-7}$ cycloalkyl.

31. The compound according to claim 10, wherein the phenyl group is meta- or para-tolyl; meta- or para-methoxyphenyl; meta- or para-fluorophenyl; meta- or para-chlorophenyl; or 3-pyridyl.

* * * * *